United States Patent [19]

Popper et al.

[11] Patent Number: 5,324,864
[45] Date of Patent: Jun. 28, 1994

[54] SYNTHESIS OF FLUOROMETHYL ETHER

[75] Inventors: Felix B. Popper, Nashua, N.H.; Gerald J. O'Neill, Arlington, Mass.; Robert J. Bulka, Merrimack, N.H.

[73] Assignee: Hampshire Chemical Corp., Lexington, Mass.

[21] Appl. No.: 993,150

[22] Filed: Dec. 18, 1992

[51] Int. Cl.$^5$ ............................................. C07C 41/01
[52] U.S. Cl. .................................................... 568/683
[58] Field of Search ........................................ 568/683

[56] References Cited

PUBLICATIONS

Soborovski et al., Zhur. Obschei, Khim, 29 pp. 1142–1143, 1959.

Hine et al., J.A.C.S. 79 pp. 5493–5496, 1957.

*Primary Examiner*—Howard T. Mars
*Attorney, Agent, or Firm*—Nields & Lemack

[57] ABSTRACT

A novel process for synthesizing difluoromethyl methyl ether for use as regrigerants and blowing agents, etc. is hereby disclosed. This process involves (1) feeding chlorodifluoromethane at a rate from about 0.5 to 5 grams of feed gas per gram of solution per minute through a sodium methoxide in methanol or basic ion exchange slurry in methanol; (2) removing the gaseous product and the unreacted chlorodifluoromethane continuously; and (3) separating difluoromethyl ether from the unreacted chlorodifluoromethane.

20 Claims, No Drawings

SYNTHESIS OF FLUOROMETHYL ETHER

BACKGROUND OF THE INVENTION

This invention relates in general to fluorinated dimethyl ethers and specifically to methyl difluoromethyl ether as a starting material for the synthesis of fluorinated dimethyl ethers.

The synthesis of difluoromethyl ether, specifically bis(difluoromethyl)ether is described by the prior art as chlorination of dimethyl ether followed by the isolation and fluorination of bis(dichloromethyl)ether. Disadvantageously, the chlorination step gives a complex mixture of chlorinated dimethyl ethers some of which are unstable and thus prevent bis(dichloromethyl)ether from being harvested efficiently via distillation. In addition other intermediates such as chloromethyl methylether and bis(chloromethyl)ether are carcinogenic.

The aforementioned problems were overcome by the prior art by employing methyl difluoromethyl ether as a starting material. This process is described by the present applicant in allowed U.S. Ser. No. 875,553 which is hereby incorporated by reference.

The reaction between a sodium alkoxide and an alkyl halide to form an ether is well known and described in standard textbooks. See *Organic Chemistry* by Fieser and Fieser, page 141, incorporated herewith by reference. However, the literature is sparse regarding fluorinated ethers. U.S. Pat. No. 2,336,921 issued to Woodstown and Park discloses a reaction between a sodium alkoxide and an alkyl halide to produce a fluorinated diethyl ether only and not a fluorinated dimethyl ether, the subject of the present invention.

The synthesis of methyl difluoromethyl ether is described however by Hine and Porter in "Methylene derivatives as intermediates in polar reaction. VIII. Difluoromethylene in the Reaction of Chlorodifluoromethane with Sodium Methoxide" published in the Journal of the American Chemical Society 79, 5493-6 (1957), hereby incorporated by reference. Hine et al describe a reaction mechanism wherein the desired difluoromethyl-methyl-ether is synthesized in a batch reaction in a fixed ratio with the by-product trimethylorthoformate, while continuously refluxing the unreacted feed.

The drawback of the aforementioned difluoromethyl methyl ether synthesis is that large amounts of trimethylorthoformate are produced by the procedure in addition to the product itself breaking down to trimethylorthoformate. Both of which contribute to decreasing the difluoromethyl methyl ether production.

Accordingly it is a primary objective of the present invention to produce a high yield of difluoromethyl methyl ether.

A further objective of the present invention is to produce a high yield of difluoromethyl methyl ether, which in turn allows for a high yield of fluorinated dimethyl ethers.

A still further objective of the present invention is to produce a fluorinated dimethyl ether without producing unstable and/or carcinogenic intermediates.

Additional objectives will become known in the remaining application.

BRIEF DESCRIPTION OF THE INVENTION

The aforementioned objectives are accomplished in an elegant and novel manner by feeding chlorodifluoromethane rapidly through a sodium methoxide in methanol solution or basic ion exchange resin in methanol solution and removing unreacted chlorodifluoromethane and the fluorinated product continuously in a gaseous form and thereby suppressing the formation of trimethylorthoformate by-product and producing a high yield of the fluorinated dimethyl ether. The by-product may be further suppressed by using an inert gas sweep and/or the addition of methylorthoformate.

DETAILED DESCRIPTION OF THE INVENTION

Fluorinated dimethyl ethers have properties which make them suitable as refrigerants and blowing agents. One synthesis mechanism for fluorinated dimethyl ethers is described by the present applicant in allowed U.S. Ser. No. 875,553, hereby incorporated by reference.

Therein difluoromethyl ether was chlorinated to give a chlorinated reaction mixture including at least one compound of the formula $CF_2HOCH_{3-z}Cl_z$, wherein z is 1, 2 or 3, which compound can readily be separated from the chlorinated reaction mixture. The chlorination of difluoromethyl methyl ether formed only three derivatives, i.e. $z=1$, $z=2$, and $z=3$. The dichloromethyl difluoromethyl ether ($z=2$) was readily separated from the chlorination reaction mixture and fluorinated, with or without such separation, to form the bis(difluoromethyl)ether. It was also disclosed that $CF_2HOCCl_3$ ($z=3$) could be separated from the chlorination reaction product and fluorinated. Alternatively, the chlorination reaction product itself could be fluorinated (without prior separation) as follows:

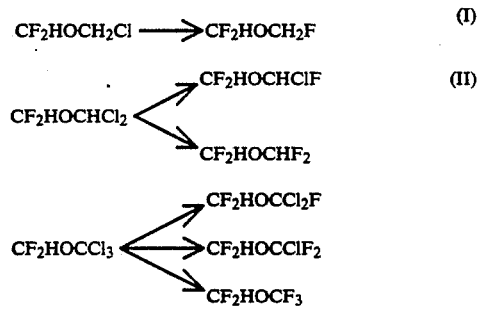

All of the above are thought useful as refrigerants, especially (I) monofluoromethyl difluoromethyl ether and (II) bis(difluoromethyl)ether, which were considered to be substitutes for R-11 and R-114 refrigerants, respectively.

In sum, the chlorination and fluorination steps of this invention were represented as:

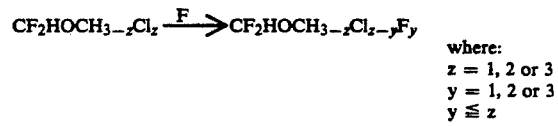

where:
$z = 1, 2$ or $3$
$y = 1, 2$ or $3$
$y \leq z$

As previously noted, difluoromethyl ether may be synthesized as described by Hine et al, by reacting sodium methoxide $NaOCH_3$ with chlorodifluoromethane ($ClF_2CH$). The prior art method involved forming an alcohol solution of sodium methoxide and bubbling the chlorodifluoromethane slowly into the reaction mixture under reflux conditions to obtain the difluoromethyl methyl ether as a residue in the reaction mixture. Unfortunately, large amounts of unwanted trimethylorthoformate by-product is produced by said method. Additionally the reaction product itself breaks down to form trimethylorthoformate. Both contribute to reducing the fluorinated dimethyl ether yield.

The present invention overcomes the prior art problems by feeding chlorodifluoromethane through a solution of sodium methoxide in methanol or a base ion exchange resin in methanol and continuously removing the unreacted chlorodifluoromethane, the product, and other gaseous compounds. Strongly and weakly basic ion exchange resins are suitable, though the reaction velocity will be greater with strong ion exchange resins. By way of illustration and not limitation mention may be made of the commercially known resins "Amberlite IRA 900" and "Amberlite IRA 93" both manufactured by the Rohm and Haas Company. Rapidly may be defined as from about 0.5 to 5 grams of feed gas per gram of solution per minute. The synthesis may be conducted at a temperature ranging from 0° to 55° C., yet preferably 5° to 45° C.

The process is preferably conducted in a batch mode or in a continuous mode yet any other process which accomplishes the same result may be substituted.

In one embodiment of the batch mode, a solution of sodium methoxide in a methanol or a suspension of ion exchange resin in methanol is preloaded into a stirred reactor. Chlorodifluoromethane is passed through the stirred liquid and the unreacted and product gases are continuously removed. The reaction is continued until a major portion of the sodium methoxide is consumed. The liquid reaction mixture is then heated to expel any dissolved product and feed gases. The resulting gases are separated by low temperature or high pressure distillation or by a combination of these; the residual chlorodifluoromethane is recycled and the product used in the next reaction step. The reactor liquid is treated to separate methanol, formed sodium chloride, or spent ion exchange resin, and trimethylorthoformate by distillation or filtration or another suitable process obvious to those skilled in the art.

In one embodiment of the continuous process, a stirred reactor is precharged with methanol and sodium methoxide, or methanol and ion exchange resin. Chlorodifluoromethane and a solution of sodium methoxide and methanol or a suspension of ion exchange resin in methanol are continuously fed to the stirred reactor. Gas is continuously removed from the process and separated as described for the batch mode; a liquid overflow is continuously removed from the stirred reactor and continuously separated as described for the batch mode.

In another embodiment of the continuous process, instead of a stirred reactor, the reactants are continuously fed through a reactor tube and then treated as described above.

The trimethylorothoformate by-product may be even further suppressed by the addition of trimethylorthoformate as a starting material, in either the batch or continuous mode. Trimethylorthoformate may be added in amounts ranging from about 0 wt. % to about 80 wt. % of the weight of the methanolic solution or slurry. The unwanted trimethylorthoformate by-product may still be further suppressed by operating under a continuous inert gas sweep with a gas such as nitrogen or helium, etc. The inert gas may be passed through at a rate from about 0 to about 90 liters of gas per liter of solution per hour, preferably from 0 to 50 liters of gas per liter of solution per hour.

The short contact time between the chlorodifluoromethane and sodium methoxide in methanol solution or the ion exchange resin suspended in methanol is critical. The desired contact time can be controlled by a number of factors, such as feed rate, temperature, and reaction pressure. By way of illustration and not limitation, a suitable feed rate ranges from about 0.5 to about 5.0 grams of feed per gram of solution per minute, and a suitable temperature ranges from about 5° C. to about 45° C. In the continuous mode the contact time may be controlled by the reaction pressure. By way of illustration and not limitation, a low superatmospheric pressure ranging from about 0 to about 40 psig may be employed, 0 to 20 psig being most preferred.

Prior Art Example (Test)

A stainless steel autoclave of 1 gallon capacity, equipped with agitator, thermowell and requisite inlet and outlet piping and valves was evacuated by a vacuum pump and 1533.1 grams of a 25% solution of sodium methoxide in methanol (383.3 grams Na methoxide; 7.10 moles) were added by suction. The autoclave was cooled to 5° C. by cold water through the autoclave cooling jacket and 320.6 grams of chlorodifluoromethane (3.70 moles) were fed to the solution over a period of 42 minutes. Despite continued cooling there was a sharp temperature rise to 32° C. in 10 minutes after feeding had commenced; at this stage, approximately 90 grams of chlorodifluoromethane had been added. The pressure rose to 25 psig. After the feed was complete, the temperature fell back to 13° C. and the pressure in the autoclave was 10 psig. The jacket temperature was raised to 30° C. over 20 minutes and the contents held for a total of 1 hour from the time the chlorodifluoromethane feed was complete.

The contents were now vented through a water condenser and the autoclave warmed to 60° C. to drive off all volatile substances. The vapor was collected in a dry ice/acetone trap at −60° to −70° C. over a 4½ hour period. The condensate in the dry ice trap was weighed, warmed to −20° C. to drive off the unreacted chlorodifluoromethane and the residue was reweighed and transferred to a small stainless steel pressure vessel via a vacuum manifold. The residual liquid in the autoclave and the gas collected in the pressure cylinder were analyzed by gas/liquid chromatography; the residual chlorodifluoromethane was determined by weight difference. The results are shown in the table below:

EXAMPLES 1 through 5

A one liter resin kettle was used to demonstrate the novel features of this invention. The resin kettle was equipped with a magnetic stirring bar, two feed dip legs, a product vent and a thermocouple pocket. It was jacketed with a water jacket. The resin kettle was charged with methanol and either sodium methoxide (1.295 moles, Examples 1–4), or a basic ion exchange resin (0.125 mole equivalent Amberlite IRA 900, Example 5). The resin kettle could be heated with water. Runs were performed by feeding chlorodifluoromethane at various amounts and rates to the kettle through one dip leg at a chosen temperature; in some runs, nitrogen was fed through the other dip leg (Examples 2, 3, and 4). Product and unreacted chlorodifluoromethane were allowed to escape continuously through the vent and the vapors so escaping were cooled and collected in a liquid nitrogen trap. At the end of the run the entire condensate was weighted and transferred to a stainless steel cylinder as described in the prior art experiment. The condensate and the liquid remaining in the resin kettle were analyzed as described above. The results are shown in the table below.

| Run | Base type* | Base moles | Freon22 (CF$_2$HCl) moles | Freon22 (CF$_2$HCl) g/min. | MOF moles | N2 l/hr | Temp. °C. | Untreated Freon Moles | Product E-152a moles | Product MOF moles | Mole ratio E/M*** | Pass yield wt % |
|---|---|---|---|---|---|---|---|---|---|---|---|---|
| Test | M | 7.00 | 3.70 | 7.66 | — | — | 4–33 | .022 | 1.979 | .626 | 3.2 | 53.3 |
| (1) | M | 1.295 | 1.654 | 2.04 | — | — | 30 | .688 | .466 | .161 | 2.9 | 74.3 |
| (2) | M | 1.295 | 1.631 | 1.93 | — | 1.5 | 30 | .803 | .408 | .130 | 3.1 | 75.8 |
| (3) | M | 1.295 | 1.595 | 1.66 | .175 | 2.1 | 30 | .791 | .465 | .098 | 4.7 | 82.6 |
| (4) | M | 1.295 | 1.569 | 2.00 | .351 | 2.1 | 30 | .738 | .469 | .037 | 12.7 | 92.7 |
| (5) | R | 0.125 | 1.234 | .38 | — | 17.0 | 55 | .143 | .024 | .004 | 6.0 | 85.7 |

*R = Amberlite IRA-300 base ion exchange resin
*M = sodium methoxide
**MOF = trimethylorthoformate. Product moles refer to difference between feed and recovered material.
***Mole ratio of recovered E-152a to trimethylorthoformate.
****E-152a = methyl difluoromethyl ether
CDF = chlorodifluoromethane The above table demonstrates the increased product yield over the prior art. Notably, in experiments 3 and 4 the yield increased even further when adding trimethylorthoformate, the unwanted by-product, as a starting material thereby suppressing its end product formation. The nitrogen sweep illustrated in examples 2, 3 and 4 also resulted in increased yield. Example 5 illustrates that the trimethylorthoformate formation was suppressed and product yield increased by the use of an ion exchange resin.

Since certain changes may be made without departing from the scope of the invention as described herein, it is intended that all matter described in the foregoing specification, including the examples, shall be interpreted as illustrative and not in a limiting sense.

We claim:

1. A process for synthesizing difluoromethyl methyl ether comprising the steps of:
   a. feeding chlorodifluoromethane at a rate from about 0.5 to 5 grams of feed gas per gram of solution per minute through sodium methoxide in methanol in the presence of trimethylorthoformate;
   b. removing the gaseous product and the unreacted chlorodifluoromethane continuously; and
   c. separating difluoromethyl ether from the unreacted chlorodifluoromethane.

2. The process described in claim 1, further comprising the step of recycling the unreacted chlorodifluoromethane as a starting material.

3. The process described in claim 1, said trimethylorthoformate is present in an amount up to about 80% by weight of the methanolic solution.

4. The process described in claim 1, further comprising the step of conducting steps a–c under a continuous inert gas sweep.

5. The process described in claim 4, wherein the inert gas is nitrogen.

6. The process described in claim 5, wherein the nitrogen is passed through the reaction solution at a rate ranging from about 0 to about 90 liters of gas per liter of solution per hour.

7. The process described in claim 1, wherein the process is conducted in a batch mode.

8. The process described in claim 1, wherein the process is conducted in a continuous mode.

9. The process described in claim 1, wherein steps a and b are carried out at a pressure ranging from about 0 to about 40 psig.

10. A process described in claim 1, wherein steps a and b are carried out at a temperature ranging from about 0° C. to about 55° C.

11. A process for synthesizing difluoromethyl methyl ether comprising the steps of:
    a. feeding chlorodifluoromethane at a rate from about 0.5 to 5 grams of feed gas per gram of solution per minute through a basic ion exchange slurry in methanol;
    b. removing the gaseous product and the unreacted chlorodifluoromethane continuously; and
    c. separating difluoromethyl ether from the unreacted chlorodifluoromethane.

12. The process of claim 11, further comprising the step of recycling the unreacted chlorodifluoromethane as a starting material.

13. The process of claim 11, further comprising the step of adding trimethylorthoformate as a starting material in an amount ranging from about 0 to about 80% by weight of the methanolic solution.

14. The process of claim 11, further comprising the step of conducting steps a–c under a continuous inert gas sweep.

15. The process of claim 14, wherein the inert gas is nitrogen.

16. The process of claim 15, wherein the nitrogen is passed through the reaction solution at a rate ranging from about 0 to about 90 liters of gas per liter of solution per hour.

17. The process of claim 11, wherein the process is conducted in a batch mode.

18. The process of claim 11, wherein the process is conducted in a continuous mode.

19. The process of claim 11, wherein steps a and b are carried out at a pressure ranging from about 0 to about 40 psig and a temperature ranging from about 0° C. to about 55° C.

20. The process described in claim 12, wherein the basic ion exchange resin is a strong or weak basic ion exchange resin.

* * * * *